United States Patent
Fox

(10) Patent No.: US 12,161,471 B2
(45) Date of Patent: Dec. 10, 2024

(54) PEDIATRIC ELECTROCARDIOGRAM ELECTRODE AND COVER

(71) Applicant: Samantha Fox, Wernersville, PA (US)

(72) Inventor: Samantha Fox, Wernersville, PA (US)

(*) Notice: Subject to any disclaimer, the term of this patent is extended or adjusted under 35 U.S.C. 154(b) by 274 days.

(21) Appl. No.: 17/242,472

(22) Filed: Apr. 28, 2021

(65) Prior Publication Data
US 2021/0338130 A1 Nov. 4, 2021

Related U.S. Application Data

(60) Provisional application No. 63/017,025, filed on Apr. 29, 2020.

(51) Int. Cl.
| | |
|---|---|
| *A61B 5/259* | (2021.01) |
| *A61B 5/274* | (2021.01) |
| *A61B 5/28* | (2021.01) |
| *A61B 5/318* | (2021.01) |
| *H01B 5/14* | (2006.01) |

(52) U.S. Cl.
CPC ............... *A61B 5/28* (2021.01); *A61B 5/259* (2021.01); *A61B 5/274* (2021.01); *A61B 5/318* (2021.01); *H01B 5/14* (2013.01); *A61B 2503/04* (2013.01)

(58) Field of Classification Search
CPC ................................ A61B 5/288; A61B 5/308
See application file for complete search history.

(56) References Cited

U.S. PATENT DOCUMENTS

| | | | |
|---|---|---|---|
| 2,660,175 A * | 11/1953 | Thrasher | A61B 5/252 248/362 |
| 3,888,240 A | 6/1975 | Reinhold et al. | |
| 3,961,623 A * | 6/1976 | Milani | A61N 1/0492 600/397 |
| 4,635,639 A * | 1/1987 | Hakala | A61N 1/38 600/509 |
| 4,653,501 A * | 3/1987 | Cartmell | A61B 5/259 600/397 |
| 4,671,591 A * | 6/1987 | Archer | H01R 11/12 439/346 |
| 4,865,566 A * | 9/1989 | Rasmussen | A61B 5/274 439/825 |
| 5,206,602 A * | 4/1993 | Baumgartner | A61B 5/30 330/258 |
| 5,265,579 A * | 11/1993 | Ferrari | A61B 5/282 600/385 |
| 6,453,186 B1 | 9/2002 | Lovejoy et al. | |
| 6,477,430 B1 * | 11/2002 | Feuersanger | A61N 1/046 607/142 |
| 8,660,630 B2 | 2/2014 | Chang | |
| 9,451,897 B2 * | 9/2016 | Mazar | A61B 5/335 |
| 2007/0276273 A1 | 11/2007 | Watson | |

(Continued)

*Primary Examiner* — Kennedy Schaetzle
(74) *Attorney, Agent, or Firm* — Boudwin Intellectual Property Law; Daniel Boudwin

(57) ABSTRACT

A pediatric electrocardiogram electrode and cover are provided. The pediatric electrocardiogram electrode and cover includes an electrode. The electrode includes an interface that is designed to connect to an electrocardiogram machine. The electrode also includes a gel surface that conducts electrical currents through the electrode. A cover is sized to cover the electrode. The electrode includes an adhesive surface to secure the cover thereon. The cover includes a pair of arms that can overlap to secure the cover to the electrode.

7 Claims, 3 Drawing Sheets

(56) References Cited

U.S. PATENT DOCUMENTS

2011/0201913 A1* 8/2011 Kim ................. A61B 5/274
  600/394
2014/0012360 A1* 1/2014 Griesser ............. A61N 1/0472
  607/142
2014/0276148 A1 9/2014 Kim

* cited by examiner

PEDIATRIC ELECTROCARDIOGRAM ELECTRODE AND COVER

CROSS REFERENCE TO RELATED APPLICATIONS

This application claims the benefit of U.S. Provisional Application No. 63/017,025 filed on Apr. 29, 2020. The above identified patent application is herein incorporated by reference in its entirety to provide continuity of disclosure.

BACKGROUND OF THE INVENTION

The present invention relates to a pediatric electrocardiogram electrode and cover. Specifically, the present invention provides an electrode that is adapted for pediatric use and a cover for use with the electrode.

Electrocardiogram machines are commonly utilized to identify and diagnose a patient's heart problems or to monitor the patient's cardiovascular health. These machines, also known as ECG or EKG machines, generate and record electrical signals in the patient's heart. Traditionally, a patient will position himself or herself on an examination table or bed, at which point a number of electrodes will be attached to the patient's chest and/or limbs. These electrodes act as sensors to determine various cardiovascular factors, including heart rate, heart rhythm, heart attack information, blood and oxygen levels, and structural abnormalities.

Standard electrodes on electrocardiogram machines, or ECG machines, have been known to cause severe skin irritation. This is due to the probe typically requiring a large adhesive base in order to secure to the chest of the patient. This is particularly problematic when dealing with children, as children generally have a smaller surface area than adults and are less likely to sit or lay still while attached to the ECG machine. Even after the electrodes are removed from the patient, the adhesive applied may take several days to completely remove from the patient's skin.

Therefore, there is a defined need in the known arts for an improved electrocardiogram electrode system that provides enhanced comfort and usability without sacrificing the underlying functionality and accuracy.

SUMMARY OF THE INVENTION

In view of the foregoing disadvantages inherent in the known types of electrode sensors and covers now present in the prior art, the present invention provides an improved pediatric electrocardiogram electrode wherein the same can be utilized for providing convenience for the user when attaching one or more electrodes to a patient undergoing an electrocardiogram.

The present system comprises an electrode. The electrode comprises an interface that is configured to connect the electrode to an electrocardiogram machine. The electrode further comprises a gel surface that conducts electrical currents through the electrode. A cover is dimensioned and adapted to cover the electrode. The electrode includes an adhesive surface to secure the cover thereon. The cover includes a pair of arms that can overlap to secure the cover to the electrode.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1A:
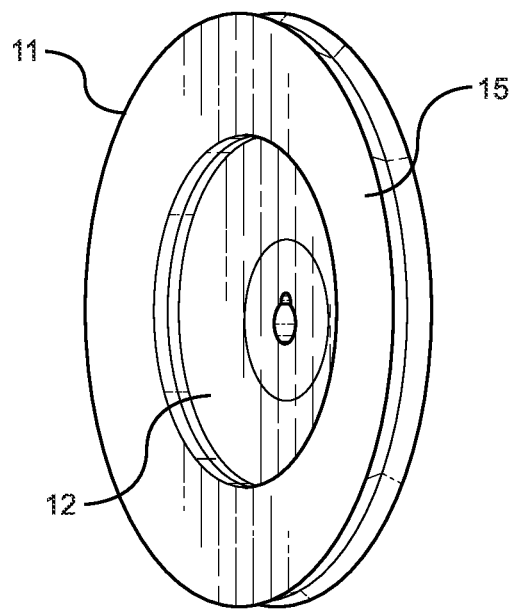
FIG. 1A shows a front view of an electrode of an embodiment of the pediatric electrocardiogram electrode.

Reference is made herein to the attached drawings. Like reference numerals are used throughout the drawings to depict like or similar elements of the pediatric electrocardiogram electrode and cover. The figures are intended for representative purposes only and should not be considered to be limiting in any respect.

Figure 1B:
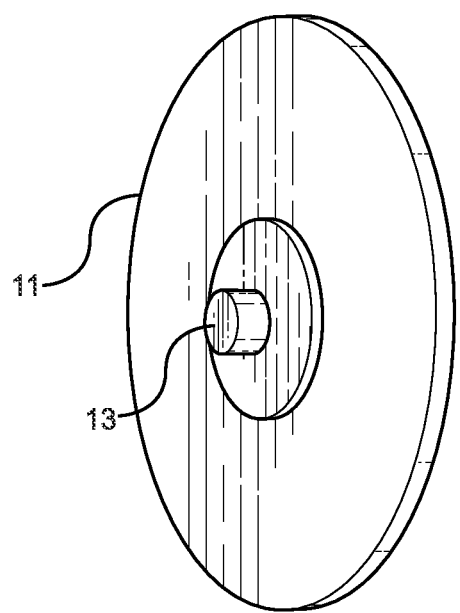
FIG. 1B shows a rear view of an electrode of an embodiment of the pediatric electrocardiogram electrode.

Referring now to FIGS. 1A and 1B, there are shown a front view and a rear view of an embodiment of the pediatric electrocardiogram electrode, respectively. The pediatric electrocardiogram comprises an electrode 11. The electrode 11 comprises a gel surface 12. The gel surface 12 is disposed within a recess defined on the front face of the electrode 11. The gel surface 12 is configured to be conductive, such as to enable the electrical signal of the electrocardiogram to pass therethrough. In the illustrated embodiment, the electrode 11 is circular. However, in alternate embodiments the electrode 11 may be of any desired shape. Furthermore, the electrode 11 is of any suitable size for use in measuring electrical signals. An adhesive portion 15 may be defined around the perimeter of the electrode 11 such as to secure the cover (shown in FIGS. 2-3) to the electrode 11.

The electrode 11 further comprises an interface 13 disposed on the rear surface of the electrode 11. The interface 13 is configured to secure the electrode 11 to a cord or wire that is connected to the electrocardiogram machine. The interface 13 is conductive in structure such that the electrical signal may pass through the interface into the gel surface 12. In the illustrated embodiment, the interface 13 is a button fastener. In some embodiments, the interface 13 may comprise an actuator to further secure the wire or cord to the electrode 11. The actuator is configured to secure the wire to the electrode 11, such that engaging the actuator allows for the electrode to be removed from the wire.

Figure 2:
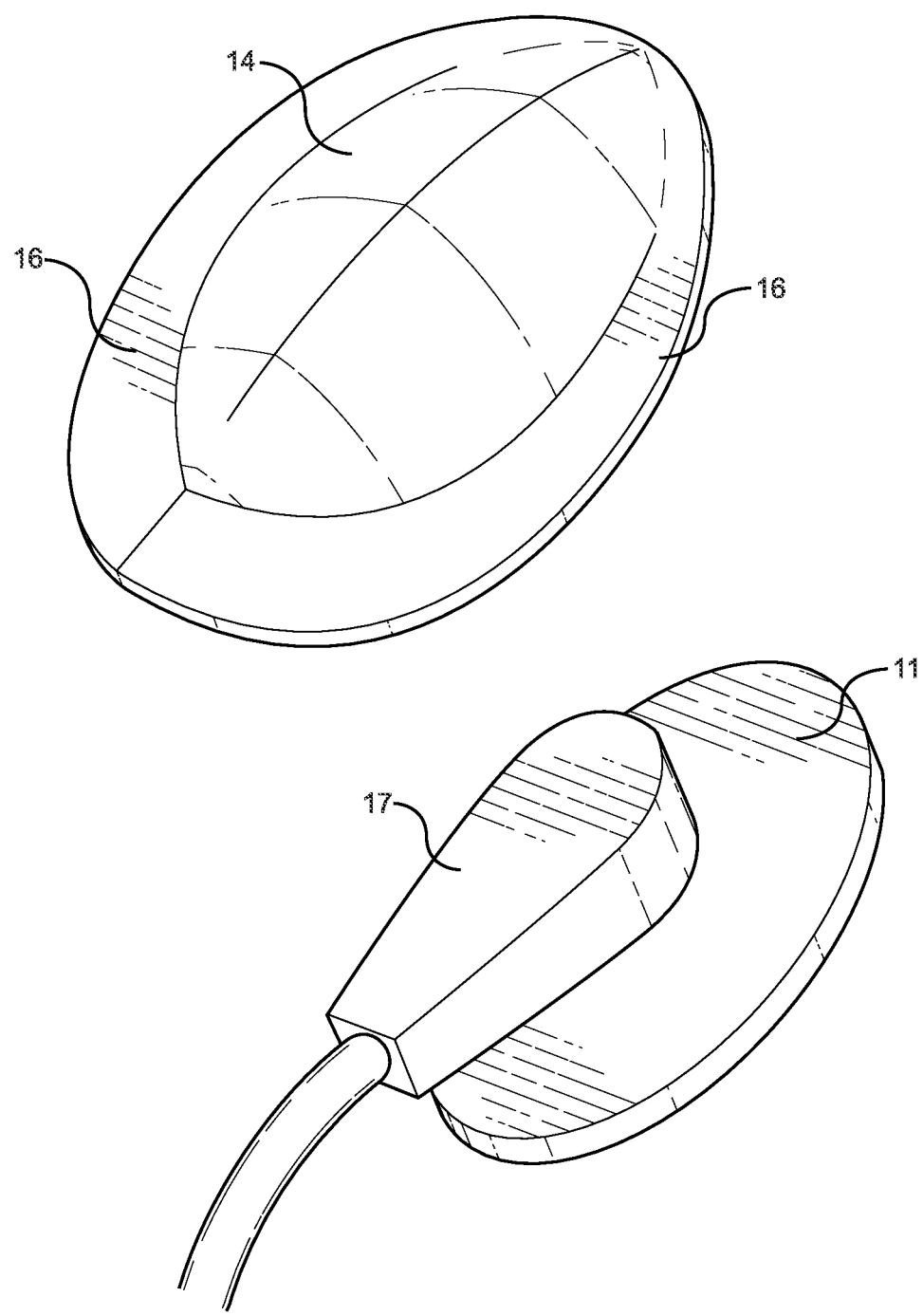
FIG. 2 shows a perspective view of an embodiment of the pediatric electrocardiogram electrode and cover.
Figure 3:
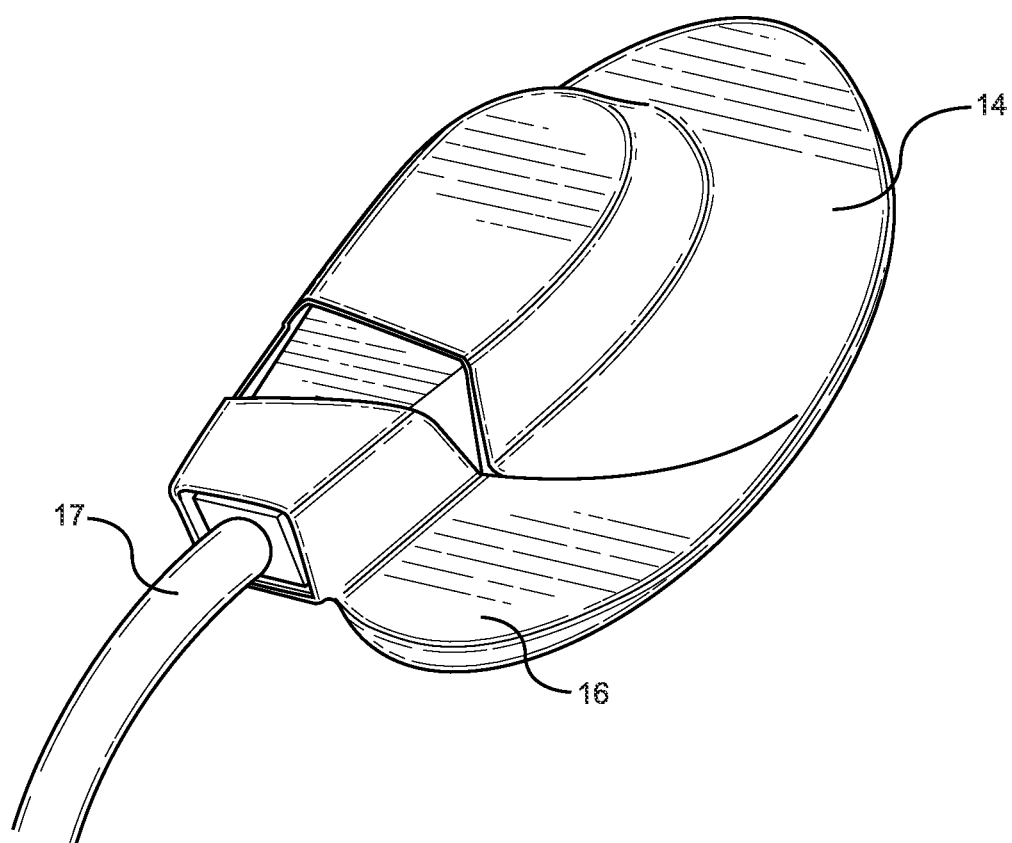
FIG. 3 shows a perspective view of an embodiment of the pediatric electrocardiogram electrode and cover.

Referring now to FIG. 2, there is shown a perspective view of an embodiment of the pediatric electrocardiogram electrode and cover. The pediatric electrocardiogram electrode further comprises a cover 14. The cover 14 is configured to attach to the electrode 11 in a manner that covers the front face of the electrode 11. The cover 14 defines a pair of tabs 16 disposed on a pair of opposing sides of the cover 14. The pair of tabs 16 are configured to separate and wrap around the electrode 11, such as to secure the cover 14 upon the electrode (as shown in FIG. 3). The cover 14 comprises an adhesive material on a front face thereof. As such, the cover 14 may be secured to the chest of the patient.

Referring now to FIG. 3, there is shown a perspective view of an embodiment of the pediatric electrocardiogram electrode and cover. In use, the pediatric electrocardiogram electrode is assembled by connecting the cord 17 to the electrode 11 (as shown in FIG. 2). The cover 14 is then placed over the electrode 11 and connecting portion of the cord 17. In one embodiment, the cover 14 defines a pocket into which the electrode 11 may be placed. Once the cover 14 is secured over the electrode 11, the pair of tabs 16 are utilized to secure the cover 14. Specifically, in the demonstrated embodiment, the right tab of the pair of tabs 16 is wrapped over the left tab of the pair of tabs 16. As such, the cover 14 will be secured upon the electrode 11. Once secured, the electrode 11 and cover 14 may be placed upon the patient for use with the electrocardiogram.

It is therefore submitted that the instant invention has been shown and described in various embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A pediatric electrocardiogram electrode, comprising:
    an electrocardiogram electrode;
    a gel surface disposed directly on the electrocardiogram electrode, the gel surface is disposed within a recess defined on the front face of the electrocardiogram electrode;
    a cover placed directly over the electrocardiogram electrode;
    wherein an interface is defined on the rear surface of the electrocardiogram electrode;
    wherein the cover comprises a pair of tabs disposed on a pair of opposing sides thereof; and
    wherein the interface is dimensioned to receive a cord connecting the electrocardiogram electrode to an electrocardiogram machine.

2. The pediatric electrocardiogram electrode of claim 1, wherein the electrocardiogram electrode is circular in shape.

3. The pediatric electrocardiogram electrode of claim 1, wherein the interface further comprises an actuator configured to secure a wire to the interface, wherein engaging the actuator enables separation of the wire from the electrocardiogram electrode.

4. The pediatric electrocardiogram electrode of claim 1, wherein the electrocardiogram electrode comprises an adhesive portion on a front section thereof.

5. The pediatric electrocardiogram electrode of claim 1, wherein the cover comprises an adhesive material on a front face thereof.

6. The pediatric electrocardiogram electrode of claim 1, wherein the interface comprises a button fastener.

7. A method of securing a pediatric electrocardiogram electrode to a patient, comprising:
    attaching a cord to an electrocardiogram electrode;
    the cord attached to an electrocardiogram machine;
    placing a cover directly upon the electrocardiogram electrode;
    securing the cover directly upon the electrocardiogram electrode using a pair of tabs; and
    attaching the electrocardiogram electrode to a desired location upon a patient.

* * * * *